United States Patent
Jackels

(10) Patent No.: US 9,943,446 B2
(45) Date of Patent: Apr. 17, 2018

(54) METHOD OF MANUFACTURING UNBONDED, ABSORBENT FIBROUS STRUCTURES

(71) Applicant: The Procter & Gamble Company, Cincinnati, OH (US)

(72) Inventor: Hans Adolf Jackels, Mechernich (DE)

(73) Assignee: The Procter & Gamble Company, Cincinnati, OH (US)

( * ) Notice: Subject to any disclaimer, the term of this patent is extended or adjusted under 35 U.S.C. 154(b) by 36 days.

(21) Appl. No.: 15/160,112

(22) Filed: May 20, 2016

(65) Prior Publication Data

US 2016/0346135 A1    Dec. 1, 2016

(30) Foreign Application Priority Data

May 28, 2015  (EP) .................................... 15169524

(51) Int. Cl.
*A61F 13/15*  (2006.01)
*D04H 1/732*  (2012.01)

(52) U.S. Cl.
CPC .. *A61F 13/15658* (2013.01); *A61F 13/15617* (2013.01); *A61F 13/15626* (2013.01); *D04H 1/732* (2013.01)

(58) Field of Classification Search
None
See application file for complete search history.

(56) References Cited

U.S. PATENT DOCUMENTS

| | | | |
|---|---|---|---|
| 3,973,291 A | 8/1976 | Kolbach | |
| 4,610,678 A * | 9/1986 | Weisman | A61F 13/15203 604/368 |
| 4,640,810 A | 2/1987 | Laursen et al. | |
| 4,767,586 A * | 8/1988 | Radwanski | D21F 9/00 264/112 |
| 4,904,439 A * | 2/1990 | Farrington | D21F 9/00 264/113 |
| 4,908,175 A | 3/1990 | Angstadt | |
| 5,316,601 A * | 5/1994 | Hebbard | A61F 13/15617 156/543 |
| 5,750,066 A * | 5/1998 | Vonderhaar | A61F 13/15658 264/510 |

(Continued)

FOREIGN PATENT DOCUMENTS

| | | |
|---|---|---|
| EP | 0 168 957 A1 | 1/1986 |
| EP | 0 252 650 A | 1/1988 |
| EP | 1 621 165 A1 | 2/2006 |

OTHER PUBLICATIONS

PCT/US2016/033980 PCT International Search Report, dated Aug. 1, 2016, 10 pages.
EP Search Report dated Nov. 30, 2015, 5 pages.

*Primary Examiner* — Mary Lynn F Theisen
(74) *Attorney, Agent, or Firm* — Charles R. Matson

(57) ABSTRACT

The present invention relates to a method of manufacturing an unbonded, absorbent, fibrous structure, the method comprising the steps of: a) providing of a first fibrous material in the form of a fibrous sheet (10); b) defiberizing the sheet (10) of first fibrous material to form a roughly graded material (16); c) mixing the roughly graded material (16) with a second material (26) to form a mixture; and d) air-laying the mixture on a foraminous carrier (50) to form the unbonded, absorbent, fibrous structure.

5 Claims, 4 Drawing Sheets

(56) References Cited

U.S. PATENT DOCUMENTS

2006/0105075 A1* 5/2006 Otsubo ............. A61F 13/15626
                                                          425/363
2009/0281511 A1* 11/2009 Fukae ............... A61F 13/15626
                                                          604/358
2013/0014899 A1* 1/2013 Nakano ............. A61F 13/15642
                                                          156/361
2014/0027943 A1* 1/2014 Hoshika ............ A61F 13/15617
                                                          264/121

* cited by examiner

METHOD OF MANUFACTURING UNBONDED, ABSORBENT FIBROUS STRUCTURES

CROSS REFERENCE TO RELATED APPLICATIONS

This application claims priority to European Application No. 15169524.4 filed on May 28, 2015, which is herein incorporated herein by reference.

FIELD OF THE INVENTION

The present invention relates to a method of manufacturing unbonded, absorbent, fibrous structures, such as absorbent pads.

BACKGROUND OF THE INVENTION

The use of fibrous structures in absorbent articles such as diapers or feminine hygienic articles is well known in the art. Fibrous structures may be either consolidated, bonded webs, such as nonwoven webs, but can also be unbonded structures, often made of natural fibers such as cellulose fibers or chemically modified cellulose fibers.

Unbonded fibrous structures can for example be used as absorbent cores, wherein the fibers are typically mixed with superabsorbent gelling materials, such as superabsorbent polymer particles. Moreover, such unbonded fibrous structures can be used in so-called liquid acquisition systems overlaying the absorbent core.

With the processes used today for high speed manufacture of fibrous webs for absorbent articles, it is difficult to make unbonded fibrous webs having a relatively low basis weight, such as basis weights below 120 g/m$^2$ as such fibrous webs typically suffer from poor homogeneity, resulting in holes in the web and low web integrity. When used in absorbent articles, holes lead to reduced integrity of the fibrous structure, which can reduce the liquid handling performance of absorbent articles.

EP-A-0 252 650, published on Jan. 13, 1988, discloses processes for making individualized, stiffened fibers. The fibers may be directly deposited on a foraminous forming wire in a manner similar to conventional pulp sheeting processes and formed into pulp sheets. Pulp sheets may be undensified or compacted. In one embodiment the individualized, stiffened fibres are combined with conventional fibres to be made into a densified pulp sheet for subsequent defibration and formation into absorbent pads. The incorporation of the conventional fibers eases dry compression of the pulp sheet into a densified form.

Whereas mixtures of fibres, such as mixtures of individualized, stiffened fibers combined with conventional fibers, can be processed into absorbent pads using the methods of the prior art, it would be desirable to provide more flexible processes in which pulp sheets can be transformed into various absorbent pads, the pads having different compositions, different profiles, different densities etc.

Thus the present invention provides a method wherein roughly graded material of first fibrous sheets having certain composition can be mixed with second material(s) after defiberising and directly prior to forming the fibrous structure or pad.

SUMMARY OF THE INVENTION

The present invention provides a method of manufacturing an unbonded, absorbent, fibrous structure, the method comprising the steps of:

a) providing of a first fibrous material in the form of a fibrous sheet;
b) defiberising the sheet of first fibrous material to form a roughly graded material;
c) mixing the roughly graded material with a second material to form a mixture; and
d) air-laying the mixture on a foraminous surface to form the unbonded, absorbent, fibrous structure.

DETAILED DESCRIPTION OF THE INVENTION

Definitions

Figure 1:
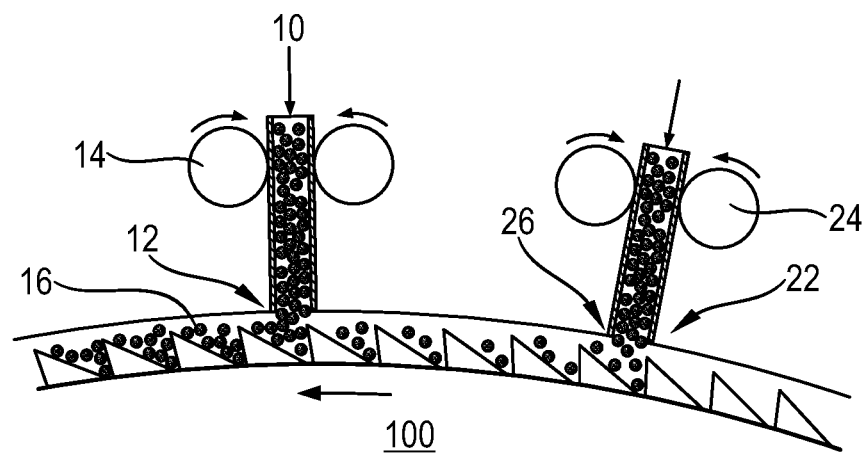
FIG. 1 is a schematic drawing of an embodiment of the present invention.

Absorbent article" refers to devices that absorb and contain body exudates, and, more specifically, refers to devices that are placed against or in proximity to the body of the wearer to absorb and contain the various exudates discharged from the body. Absorbent articles may include diapers, pants, training pants, adult incontinence undergarments, feminine hygiene products, and the like. As used herein, the term "body fluids" or "body exudates" includes, but is not limited to, urine, blood, vaginal discharges, breast milk, sweat and fecal matter. Preferred absorbent articles of the present invention are diapers, pants, training pants and feminine hygiene products such as sanitary napkins and/or sanitary pads "Absorbent core" means a structure typically disposed between a topsheet and a backsheet of an absorbent article for absorbing and containing liquid received by the absorbent article. The absorbent core typically comprises absorbent material such as airfelt (comprising cellulose fibers), superabsorbent particles, or absorbent foams. In one embodiment, the absorbent core may be substantially cellulose free (i.e. less than 1% cellulose) and may comprise one or more substrates, absorbent polymer material disposed on the one or more substrates, and a thermoplastic composition on the absorbent particulate polymer material and at least a portion of the one or more substrates for immobilizing the absorbent particulate polymer material on the one or more substrates. In a multilayer absorbent core, the absorbent core may also include a cover layer. The one or more substrates and the cover layer may comprise a nonwoven. For the present invention, the absorbent core does not include an acquisition system, a topsheet, or a backsheet of the absorbent article.

"Absorbent polymer material," "absorbent gelling material," "AGM," "superabsorbent," and "superabsorbent material" are used herein interchangeably and refer to cross linked polymeric materials that can absorb at least 5 times their weight of an aqueous 0.9% saline solution as measured using the Centrifuge Retention Capacity test (Edana 441.2-01).

"Absorbent particulate polymer material" is used herein to refer to an absorbent polymer material which is in particulate form so as to be flowable in the dry state.

"Diaper" refers to an absorbent article generally worn by infants and incontinent persons about the lower torso so as to encircle the waist and legs of the wearer and that is specifically adapted to receive and contain urinary and fecal waste. As used herein, term "diaper" also includes "pants" which is defined below.

"Pant" or "training pant", as used herein, refer to disposable garments having a waist opening and leg openings designed for infant or adult wearers. A pant may be placed in position on the wearer by inserting the wearer's legs into the leg openings and sliding the pant into position about a wearer's lower torso. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened). While the terms "pant" or "pants" are used herein, pants are also commonly referred to as "closed diapers," "prefastened diapers," "pull-on diapers," "training pants," and "diaper-pants".

A "nonwoven web" is a manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers have diameters ranging from less than about 0.001 mm to more than about 0.2 mm and they come in several different forms such as short fibers (known as staple, or chopped), continuous single fibers (filaments or monofilaments), untwisted bundles of continuous filaments (tow), and twisted bundles of continuous filaments (yarn). Nonwoven fabrics can be formed by many processes such as meltblowing, spunbonding, solvent spinning, electrospinning, carding and airlaying. The basis weight of nonwoven fabrics is usually expressed in grams per square meter (gsm).

"Roughly graded material" as used herein refers to fibrous material, wherein the majority of the fibers are not individualized. Thus, the majority of the fibers are present as clusters in the roughly graded material. A fiber cluster as used herein is an aggregation of several fibers (several hundreds up to several thousand fibers). The fiber clusters may have a diameter of only a few millimeters or have a diameter of up to several centimeters, e.g. up to 5 cm, depending how well the fiber clusters have been isolated and taken out from the raw material, which is typically provided in densely packed bales.

The method of the present invention is illustrated in FIG. 1. A toothed cutter 100 is passed across the surface, preferably the end surface, of a fibrous sheet 10 comprising first fibrous material. Preferably the fibrous sheet 10 has a bulk density in the range from 0.1 to 0.85 g/cm$^3$. The sheet 10 is advanced into the first cutting zone 12 by a first feeding device 14, at a first feed rate. The cutter 100 breaks the sheet into roughly graded material 16 and transports the roughly graded material 16 away from the cutting zone 12.

A second material 26 is fed into a second cutting zone 22 by a second feeding device 24, at a second feed rate. Preferably the second material 26 has a bulk density in the range from 0.1 to 0.85 g/cm$^3$. The first feed rate and the second feed rate need not be the same. Indeed it is an advantage of the present invention that the ratio between first feed rate and the second feed rate can be preselected in order to provide different absorbent pads containing different proportions of the first fibrous material and the second material.

In FIG. 1 the second material 26 is shown as a material in sheet form 20. However for the purpose of the invention the second material 26 may be fed to the cutter 100 in any suitable physical form, not limited to a sheet.

Figure 2:
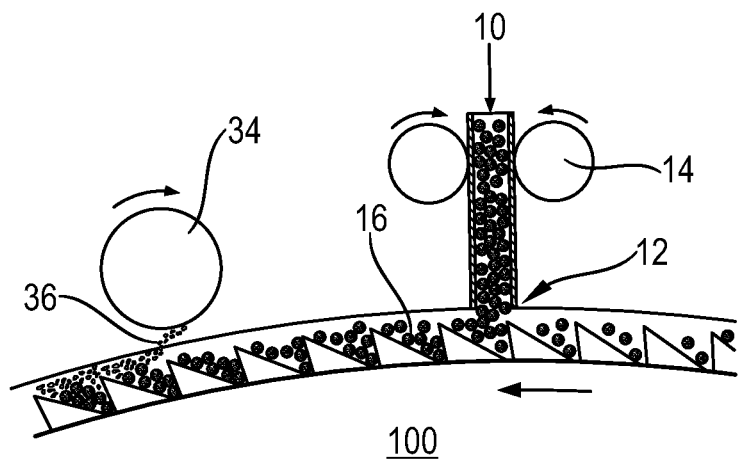
FIG. 2 a schematic drawing of another embodiment of the present invention.

In FIG. 2 the second material 36 is fed to the cutter 100 by means of a rotating drum 34 which meters the feed rate of the second material 36. Such an arrangement is particularly suitable for the addition of material in particulate form, such as absorbent particulate polymer material. Suitable rotating drum metering systems are disclosed in EP-A-1 621 165, published on Feb. 1, 2006, entitled "Indirect Printing of AGM".

The embodiments of FIGS. 1 and 2 may be combined in order to provide mixtures of the roughly graded first fibrous material 16 with more than one second material 26, 36, in which case the added materials will be referred to as the second, third, fourth, etc. materials.

Examples of second, third, fourth, etc. materials are absorbent materials, for example absorbent particulate polymer material; cellulose fibers, for example air felt, or individualized, stiffened fibers; and other staple fibers, preferably from 0.5 mm to 10 mm long. In one embodiment of the present invention these materials comprise a mixture of individualized, stiffened fibers, such as those described in EP-A-0 252 650, with eucalyptus fibers, for example at a ratio of 90:10. In a preferred embodiment of the present invention the first fibrous material comprises individualized, stiffened fibers, such as those described in EP-A-0 252 650.

Defiberising

The cutter 100 breaks up the first fibrous sheet in a roughly graded material 16. This step is referred to herein as a defibration step, or defiberising. Preferably the cutter is a toothed cutter, more preferably a rotary, toothed cutter. Such a cutter may take the form of a drum with teeth positioned around the circumferential surface of the drum.

The roughly graded first material is combined at the teeth of the cutter 100 with the second, third, fourth etc., materials and subsequently transported by the cutter 100 to a transfer zone. At the transfer zone the combined materials are air laid on a foraminous carrier 50.

Transfer

Figure 3:
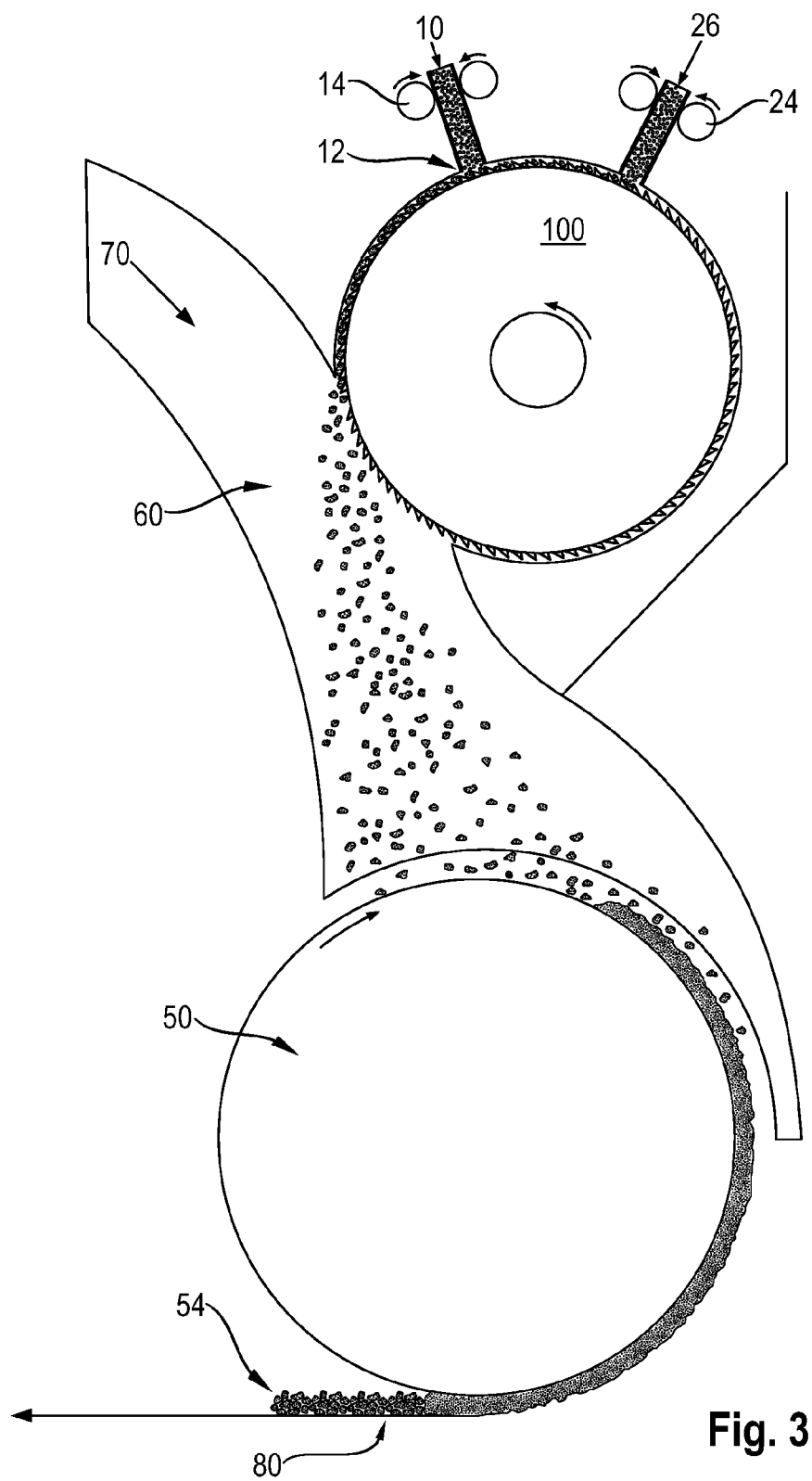
FIG. 3 is a schematic drawing of an embodiment of the present invention, including the laydown section.
Figure 4:
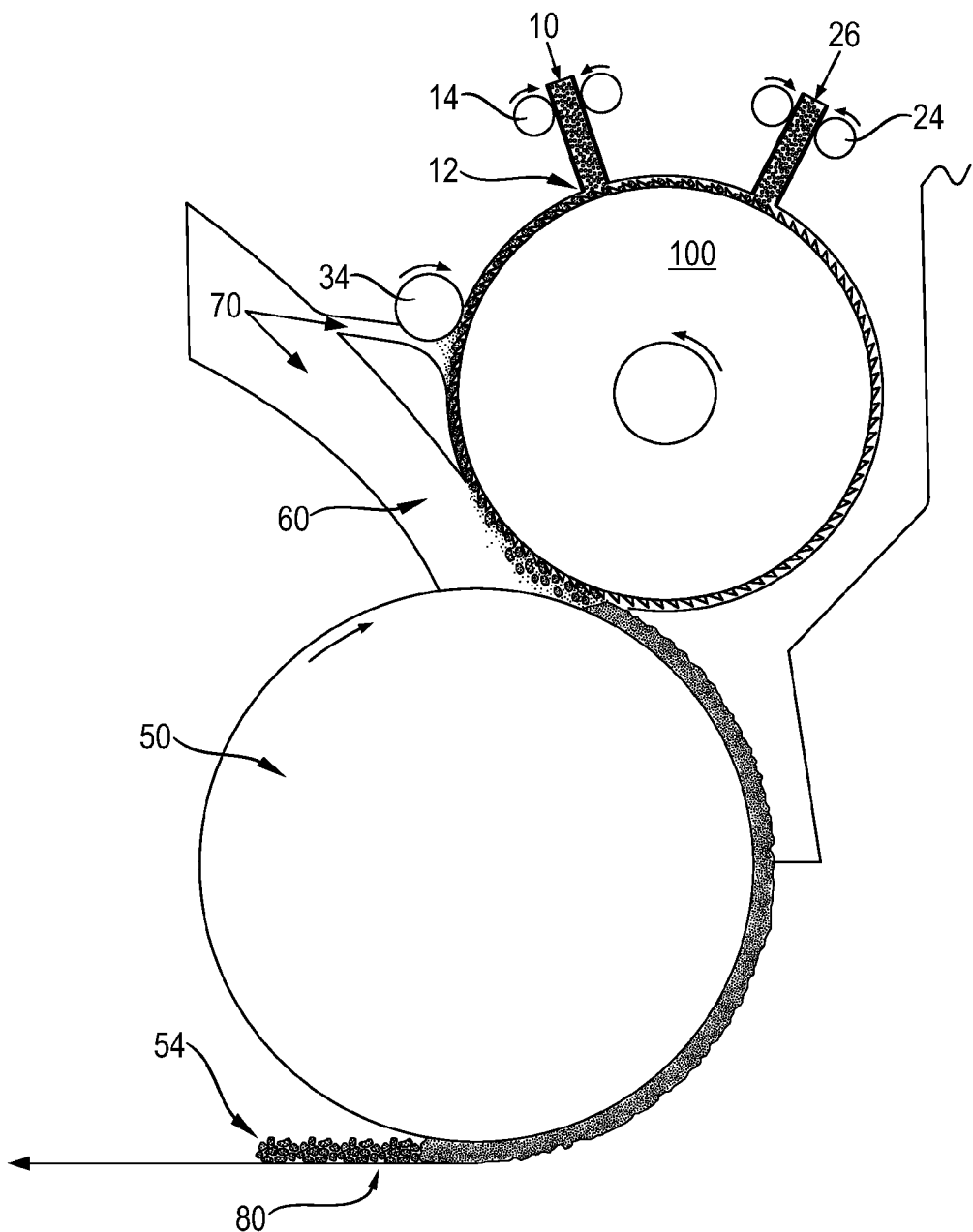
FIG. 4 is a schematic drawing of another embodiment of the present invention, including the lay-down section.

FIGS. 3 and 4 show different embodiments of the transfer of the combined materials from the cutter 100 to the foraminous carrier 50 via a transfer duct 60.

Preferably the combined materials on the cutter 100 are blown off from between the teeth of the cutter by blow-off air supplied under pressure from within the cutter 100, and/or the combined materials may be sucked off from between the teeth of the cutter by providing a region of lower pressure of air within the transfer duct 60. The air pressure within the transfer duct 60 may be reduced, for example, by means of baffles, or by aerodynamic surfaces which reduce the pressure by a Bernoulli effect.

A foraminous carrier 50 may be of any suitable design enabling fibers to be deposited on its upper surface, and then capable of delivering the fibrous structure thus formed to a subsequent station. In one embodiment the foraminous carrier 50 is configured as an endless belt. In another embodiment, the foraminous carrier 50 is configured in form of a drum. In the latter embodiments it is desirable that the drum-shaped foraminous carrier 50 has a diameter of from 400 mm to 800 mm, or from 500 mm to 600 mm. The drum 50 is placed such that the axis of the foraminous carrier drum 50 is positioned essentially horizontally. A drum-shaped foraminous carrier 50 is illustrated in FIGS. 3 and 4. In these embodiments, the pressure differential is applied for example by applying low-pressure or vacuum within the drum-shaped foraminous carrier. The fibers are deposited on the part of the outer surface of the foraminous carrier 50, which is adjacent the cutter 100. Due to the rotation of the drum-shaped foraminous carrier 50 the fibrous structure is moved downward while still held on the surface of the foraminous carrier 50 by the low-pressure or vacuum applied inside the drum-shaped foraminous carrier 50. Once the fibrous structure has reached a more downward position, it passes a zero pressure (i.e. no pressure differential between the inside and the outside of the drum) or overpressure zone (i.e. a higher pressure inside the drum compared to outside of the drum), which enables the fibrous structure to be transferred from the drum-shaped foraminous carrier 50 onto another carrier 80 which is located below the drum-shaped foraminous carrier 50, such as an endless belt. On this carrier 80 the fibrous structure will again be held by applying a pressure differential, for example with a suction box underneath.

In one embodiment, the fibrous structure is placed on top of another structure, such as a nonwoven web, a film or a multiplicity of webs and/or films. In these embodiments, the all layers will be held on the carrier due to an applied pressure differential. The fibrous structure can also be placed on top of a not yet finally assembled absorbent article. The term "not yet finally assembled" as used herein means that one or more layers or components (e.g. the fastening system or parts thereof; the topsheet, the backsheet, the absorbent core, the side panels or combinations thereof) of the absorbent article are still missing and will only be joined and/or attached to the absorbent article at a subsequent, downstream stage after the fibrous structure of the present invention has been placed on the not yet finally assembled absorbent article.

If the fibrous web forms part of a multi-layer acquisition system in an absorbent article, the fibrous web may be placed on top of the one or more other layers of the acquisition system, such as a nonwoven web. For example, if the fibrous structure is used as the lower layer of an acquisition system of an absorbent article, the fibrous structure is applied on top of the upper layer of the acquisition system. The thus assembled acquisition system will subsequently be delivered to and assembled with the remaining layers and components of the absorbent core or absorbent article.

In all these embodiments, the assembled layers and/or components will be held on the foraminous carrier 50 due to an applied pressure differential.

However, in another embodiment, the fibrous structure is formed directly on the surface of the foraminous carrier 50 with no additional layers underneath.

Importantly, in such a system, the fibrous structure does not need to be wound up on a roll for intermediate storage but is immediately further processed and incorporated into the final absorbent article. Therefore, it is not necessary to consolidate and reinforce the fibrous structure for storage (for example by having an additional bonding step by thermal bonding, pressure bonding, resin bonding, adhesive bonding, needle punching, hydroentangeling, or combinations thereof). Instead, the unbonded fibrous structure, having relatively low integrity due to the absence of any consolidation step, can be directly introduced onto the absorbent core or absorbent article.

The fibrous structure can be adhesively attached to the layer or layers onto which it is deposited. Adhesive attachment can be done by gluing the complete surface of the fibrous structure to the underlying layer or layers or by only gluing selected portions of the surface. Gluing can for example be done by applying the glue in a stripe, spiral, dot or any other pattern. However, it will be sufficient to use relatively low amounts of glue, since it should be avoided that the adhesive penetrates into the fibrous structure or the underlying layer or layers as such penetration will have an adverse effect on the absorption properties.

Also, the fibrous structure is preferably only cut transversely (i.e. in cross machine direction), once the fibrous structure has been placed on one or more other layers, either on the foraminous carrier 50 or at a later stage, e.g. on carrier 80. Thereby, the fibrous structure is stabilized to certain degree, reducing the risk of damaging the fragile fibrous structure upon cutting. To enable in-line production of the fibrous structure with the manufacture of the absorbent article, in which it is used, it is desirable that the manufacture of the fibrous structure takes place at the same speed or about the same speed as the manufacture of the absorbent article as a whole. As modern absorbent article production lines often produce 1200 absorbent articles per minute or even more, this requires manufacturing speeds of the fibrous structure ranging from 200 to 350 m/min.

To enable fast and easy transfer of the fibrous structure to the absorbent article, the fibrous structure needs to have its final width already upon formation of the fibrous structure. This eliminates the need for any subsequent cutting steps along the longitudinal direction of the fibrous structure (i.e. in machine direction). Especially as the fibrous structure alone has low integrity due to the absence of any consolidation steps, cutting in the longitudinal direction bears the risk of damaging the fibrous structure. According to the present invention, the fibrous structure therefore does not undergo any longitudinal cutting (i.e. in the machine direction). The width of the fibrous structure of the present invention is from 4 cm to 25 cm, or from 5 cm to 15 cm, or from 5 cm to 12 cm.

Compared to traditional production lines for fibrous structures, which only need to accommodate the equipment for the manufacture of the fibrous structure, production lines of absorbent articles need to accommodate numerous other equipment required to manufacture or supply, and assemble all the different components of the absorbent article. Thus, absorbent article manufacturing lines have considerable higher space constraints compared to traditional production lines for fibrous structures. Therefore, it is advantageous to have a foraminous carrier 50 in form of a drum as such a carrier is less space consuming compared to a horizontal carrier.

In FIG. 3 the configuration is shown in which the end surface of a fibrous sheet 10 comprising first fibrous material is advanced into the first cutting zone 12 by a first feeding device 14, at a first feed rate. The cutter 100 breaks the sheet into roughly graded material 16 and transports the roughly graded material 16 away from the cutting zone 12. A second material 26 is fed into a second cutting zone 22 by a second feeding device 24, at a second feed rate. The first and second materials are combined at the cutter 100 and transferred via a transfer duct 60 to the foraminous carrier 50. Air is blown 70 into the transfer duct 60 to assist transfer.

In FIG. 4 the configuration is shown in which the first 16 and second 26 materials are supplemented by a third material 36. In this embodiment the third material is an absorbent gelling material in the form of particles.

In FIGS. 3 and 4 the process may be further modified to enable a variation in the unbonded fibrous structure 54. In particular the variation may correspond in the machine direction to the pitch of the unbonded fibrous structure 54 so that the first, second (optionally third, fourth etc.) materials are distributed in a desired predetermined manner. For example the first feeding device 14 and/or the second feeding device 24 (optionally third, fourth feeding devices etc.) may be driven are variable speed, for example with sinusoidal speed profile in which one speed cycle corresponds to the pitch of the unbonded fibrous structure 54. The variable drive mechanism may be, for example, servomotor or cam driven (drive mechanism not shown in FIGS. 3, 4).

The fibrous web can also be deposited on the foraminous carrier 50 in a shaped form, i.e. the longitudinal side edges of the fibrous structure do not form a straight line but take a certain shape, typically a curved shape. This can be facilitated e.g. by not having the complete surface of the carrier 50 being foraminous but by masking certain areas along the side edges of the carrier surface. Thereby, the fibers leaving the apertured, cylindrical drums are only directed towards those areas of the carrier surface which is foraminous due to the low-pressure applied below the foraminous carrier 50.

Shaped fibrous structures may be desirable in absorbent articles to facilitate a narrow crotch portion of the absorbent article. Thus, if the fibrous structure is used in an acquisition system, as absorbent core or as part of an absorbent core, the part of the fibrous structure having a narrower width will be placed in the crotch region while the parts having a wider width are placed in the front and back waist region.

Figure 5:
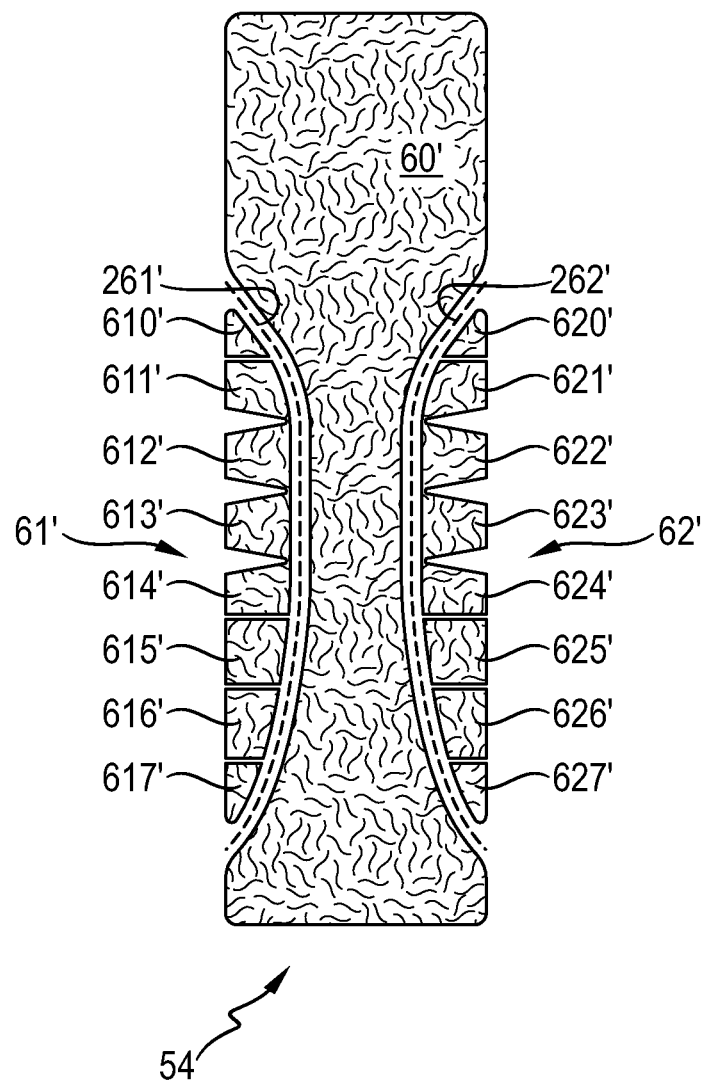
FIG. 5 is a plan view of an unbonded fibrous structure.

FIG. 5 shows an example of an unbonded fibrous structure 54 which may generally follow the contour and construction of the absorbent core over which it is disposed, although it may also be in general shorter in longitudinal and/or transversal direction. In general, the same features disclosed previously for the central portion, side portions and folding guides of the core can apply to the liquid management layer. The layer 54 may thus comprise a central portion 60' generally longitudinally extending, but which may be shorter than the central portion of the core, and two folding guides 261', 262'. These folding guides may comprise areas substantially free of the liquid management material, in this case substantially free of unbound or loosely bound hydrophilic fibers such as cross-linked cellulosic fibers. The liquid management side portions 61', 62' may further comprise winglets 610'-617', 620'-627', which as shown may correspond in shape and configuration to the winglets 610-617, 620-627 of the absorbent core, although this is not required.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of manufacturing an unbonded, absorbent, fibrous structure, the method comprising the steps of:
   providing a rotary toothed cutter comprising a first cutting zone and a second cutting zone;
   advancing a first fibrous sheet into the first cutting zone by a first feeding device at a first feed rate to defiberize the first fibrous sheet and form first roughly graded material;
   advancing a second fibrous sheet into the second cutting zone by a second feeding device at a second feed rate to defiberize the second fibrous sheet and form second roughly graded material, wherein the second feed rate varies sinusoidally with respect to time;
   mixing the first roughly graded material with the second roughly graded material to form a mixture; and
   air-laying the mixture on a foraminous carrier to form the unbonded, absorbent, fibrous structure.

2. The method of claim 1, wherein the first feed rate is not equal to the second feed rate.

3. The method of claim 1, wherein the first feed rate is a variable feed rate.

4. The method of claim 1, wherein the first fibrous sheet has a bulk density in the range from about 0.1 to about 0.85 g/cm$^3$.

5. The method of claim 1, wherein the second fibrous sheet has a bulk density in the range from about 0.1 to about 0.85 g/cm$^3$.

* * * * *